United States Patent
McMahen et al.

[11] Patent Number: 5,835,983
[45] Date of Patent: Nov. 10, 1998

[54] HEATING DEVICE AND METHOD OF MANUFACTURING THE SAME

[75] Inventors: Kelly A. McMahen, Oxford, Conn.; Charles W. Murin, Hattiesburg, Miss.; Donald S. Malin, Chicago, Ill.

[73] Assignee: Sunbeam Products, Inc., Delray Beach, Fla.

[21] Appl. No.: 713,440

[22] Filed: Sep. 13, 1996

[51] Int. Cl.$^6$ .............................. H05B 3/06; F24D 19/02; A61F 7/00; A47C 21/04

[52] U.S. Cl. ........................... 219/527; 338/59; 392/435; 607/98; 5/421

[58] Field of Search ..................... 219/211, 212, 219/217, 527, 528, 530, 540, 546, 548; 338/55, 56, 59; 392/435–437, 496; 607/96, 98, 112, 114; 137/341; 5/421, 422

[56] References Cited

U.S. PATENT DOCUMENTS

| | | |
|---|---|---|
| 2,590,212 | 3/1952 | Samuels ..................................... 607/96 |
| 2,749,914 | 6/1956 | Braley . |
| 3,114,825 | 12/1963 | Kilburn et al. . |
| 3,854,156 | 12/1974 | Williams ..................................... 5/422 |
| 4,201,218 | 5/1980 | Feldman et al. ........................... 607/114 |
| 4,429,215 | 1/1984 | Sakai et al. ................................ 219/528 |
| 4,561,441 | 12/1985 | Kolodziej . |
| 4,591,694 | 5/1986 | Phillips ..................................... 219/217 |
| 4,717,812 | 1/1988 | Makita ..................................... 219/528 |
| 4,777,346 | 10/1988 | Swanton, Jr. . |
| 4,868,898 | 9/1989 | Seto . |
| 4,920,964 | 5/1990 | Francis, Jr. . |
| 4,953,550 | 9/1990 | Dunshee . |
| 4,964,402 | 10/1990 | Grim et al. . |
| 4,993,409 | 2/1991 | Grim . |
| 5,081,339 | 1/1992 | Stine . |
| 5,245,938 | 9/1993 | Frye . |
| 5,302,807 | 4/1994 | Zhao ..................................... 219/549 |
| 5,329,096 | 7/1994 | Suematsu ............................... 219/528 |
| 5,371,340 | 12/1994 | Stanfield ................................ 219/217 |
| 5,451,747 | 9/1995 | Sullivan . |

*Primary Examiner*—Teresa J. Walberg
*Assistant Examiner*—Sam Paik
*Attorney, Agent, or Firm*—Thorp, Reed & Armstrong

[57] ABSTRACT

A multi-layered heating device including a first container having a top layer and a bottom layer. A second container, containing heat retaining fluid, is positioned inside the first container and adjacent to the top layer thereof. Adjacent to the second container is an electrical heating element, and a layer of padding material is positioned between the electrical heating element and the bottom layer of the first container. A preferred embodiment of the heating device includes at least one thermostat, with the second container having a first layer and a second layer wherein at least one portion of each of the layers are secured together to form at least one depression which is devoid of the heat retaining fluid and which coincides with the at least one thermostat.

17 Claims, 4 Drawing Sheets

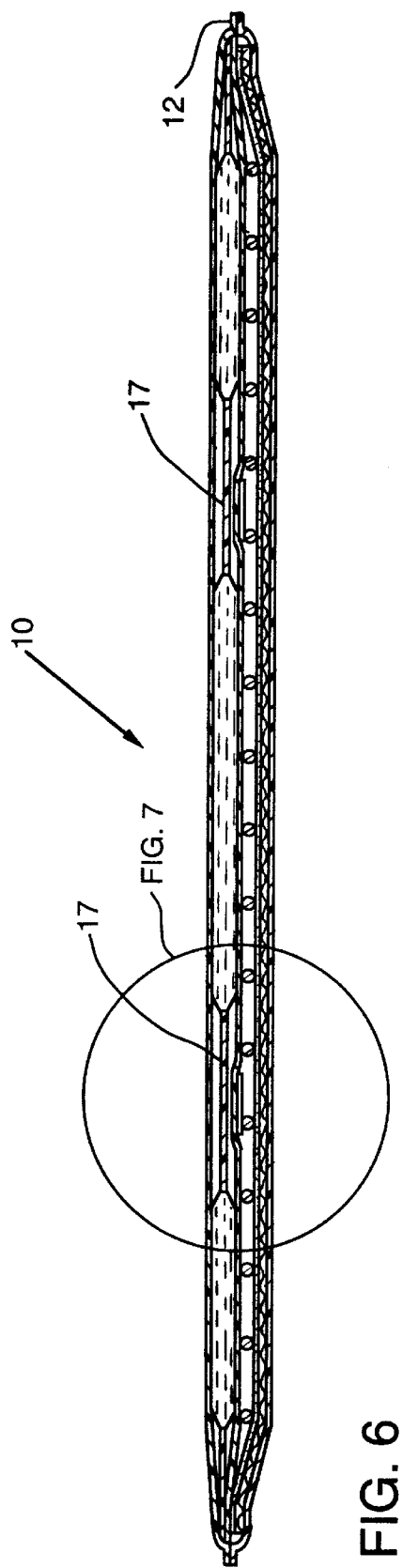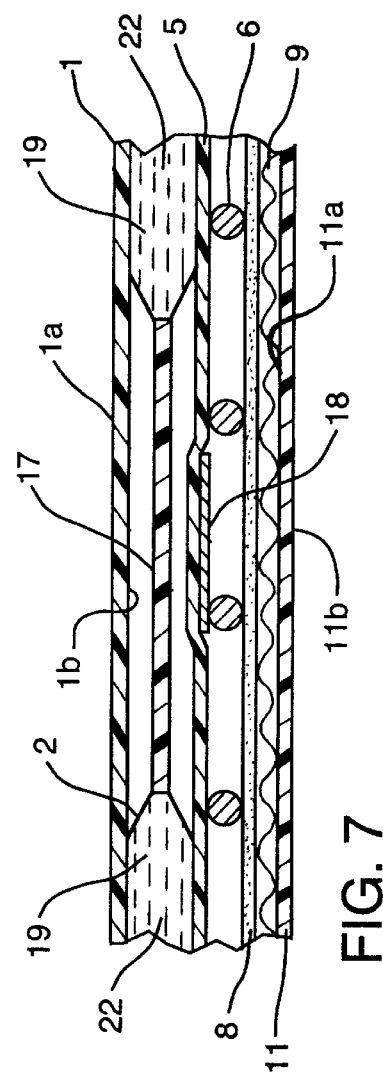
FIG. 6
FIG. 7

HEATING DEVICE AND METHOD OF MANUFACTURING THE SAME

FIELD OF THE INVENTION

This invention relates to electrically heated thermal fluid-filled heating devices and their method of manufacture. More particularly, this invention relates to a heating device having an internal fluid-filled container that is heated by means of an electric heating element contained within the heating pad.

BACKGROUND OF THE INVENTION

Heat retaining fluid-filled heating devices are known in the art. It is known that a heat retaining fluid-filled container provides additional comfort to the user of the heating device, and also provides a means by which heat is more efficiently retained for continued use after the heat source has been discontinued. A number of such prior art heating pads are designed for supplying heat therapy to various parts of the body, including the head (U.S. Pat. No. 4,777,346 to Swanton, Jr.), limbs (U.S. Pat. No. 4,964,402 to Grim, et al.) or back (U.S. Pat. No. 4,993,409 to Grim). Some prior art heated pads focus more on providing comfort and convenience rather than heat therapy. An example of such a device is a non-therapeutic heated seat disclosed in U.S. Pat. No. 4,868,898 to Seto.

The relative degree of complexity of the prior art heat retaining fluid-filled heating devices range from simple to complex. Some prior art heating devices have heat retaining material which is heated in a simple fashion by external means such as boiling water or a microwave oven. Examples of such devices are disclosed in U.S. Pat. Nos. 4,920,964 to Frances. Jr., 5,245,938 to Frye and 4,953,550 to Dunshee.

Prior art heating devices which include an electrical heating means contained within the device have a greater degree of design complexity. Examples of electrically heated fluid-filled devices are found in U.S. Pat. Nos. 4,561,441 to Kolodiej and 4,868,898 to Seto, both of which disclose a heat retaining fluid absorbed by a sponge-like material along with an internal electrical heating element enclosed within a casing. Another example of a heating pad containing an internal electrical heating element is found in U.S. Pat. No. 4,777,346 to Swanton. Jr., which discloses a fluid-filled casing retained in a second casing, with the space between the casings filled with electrically conductive foam. Some of these heating devices include internal padding material that provides additional comfort for the user and serves as insulation between the heating element and the outer surfaces of the heating device. Because the padding material is evenly distributed throughout these devices, both sides of the devices are capable of being maintained at the same outside temperature during all stages of the heating cycle.

There are several disadvantages associated with the prior art electrical heating devices having internal heating elements. First, the design complexity of these devices generally prevents their internal components from being manufactured separately, thus requiring a single production line and sophisticated assembly techniques. This lack of manufacturing flexibility has proven to be very undesirable from cost, time and supply distribution standpoints. Second, the prior art devices that use padding material have been unable to benefit therefrom without suffering from a reduction in thermal efficiency due to the thermal resistance of the padding material.

As such, it can be appreciated that there exists a continuing need for new and improved heating devices which can be more efficiently manufactured and are designed to provide comfort and insulation without loss of thermal efficiency.

SUMMARY OF THE INVENTION

The present invention provides an improved heating device and method of manufacture thereof which solves the above-mentioned problems associated with prior art heating devices.

The multi-layered heating device of the present invention comprises a first container having a top layer and a bottom layer which are secured together to form a first inner recess. A second container containing a heat retaining fluid is positioned inside the first inner recess and adjacent the top layer of the first container. Also enclosed inside the first container is an electrical heating element positioned adjacent the second container for heating the heat retaining fluid. Padding material is positioned between the electrical heating element and the bottom layer of the first container.

In a preferred embodiment, the heating device includes at least one thermostat, and the second container has a first layer and a second layer which are secured together to form a second inner recess for containing the heat retaining fluid. At least one portion of each of the first layer and the second layer of the second container are secured together to form at least one depression which is devoid of the heat retaining fluid and which coincides with the at least one thermostat.

The present invention provides a heating device that has a large degree of manufacturing flexibility due to its multi-layered design, and that has the insulation and comfort benefits of padding material without an undesirable loss in thermal efficiency.

Other details and advantages of the present invention will become apparent from the following detailed description of the presently preferred embodiments of practicing the invention.

BRIEF DESCRIPTION OF THE DRAWINGS

In the accompanying drawings, preferred embodiments of the invention and preferred methods of practicing the invention are illustrated in which:

FIG. 6 is a cross sectional view of the heating device.

FIG. 7 is an enlarged view of the cross section shown in FIG. 6.

DETAILED DESCRIPTION OF THE PREFERRED EMBODIMENT

Although the description contained herein is addressed mainly to heating pads, it should be noted that the present invention may be used in various forms of heating devices including, but not limited to, electric heating blankets, cushions, pillows and seats.

Figure 1:
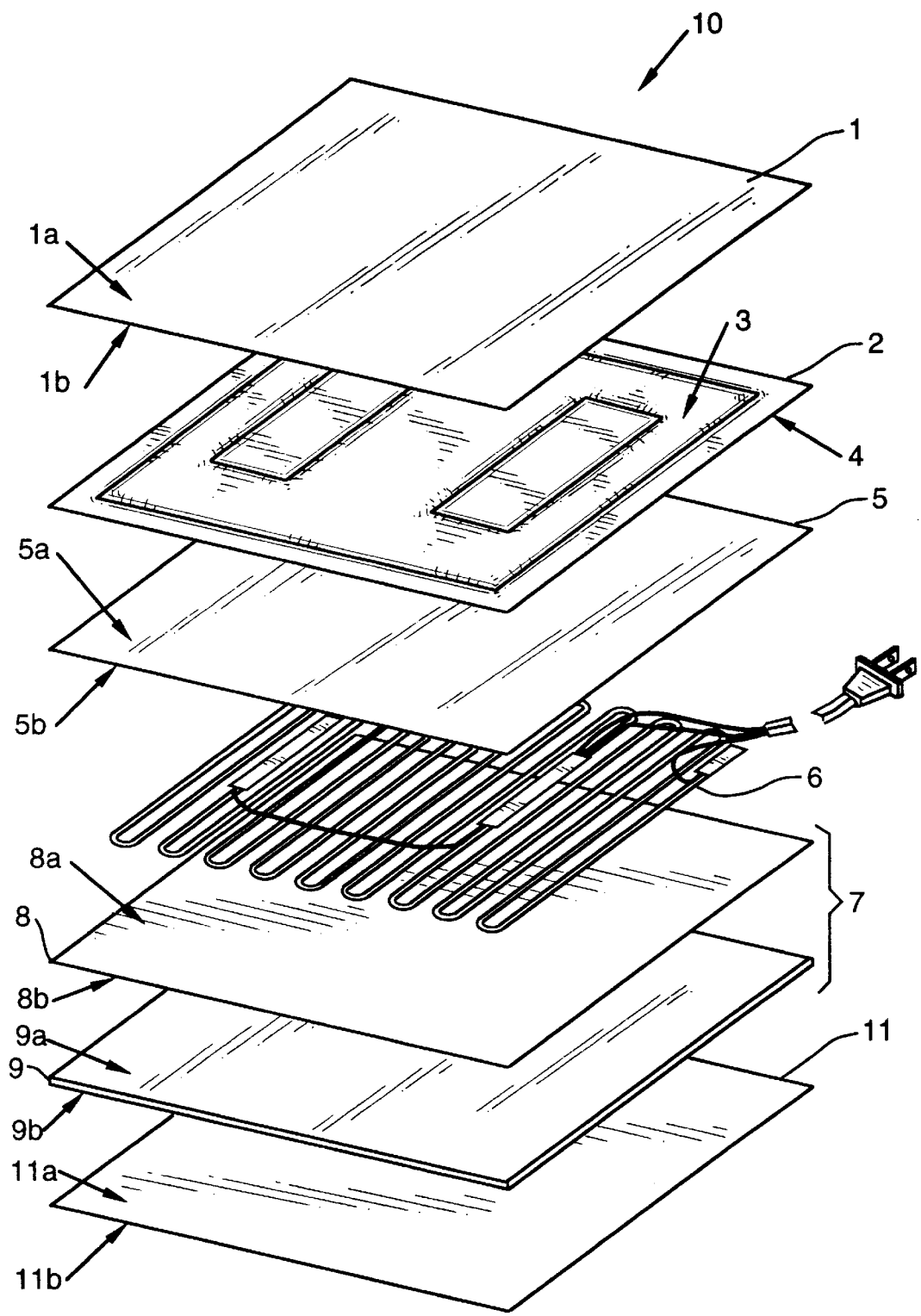
FIG. 1 is an exploded view of the heating device of the present invention.
Figure 2:
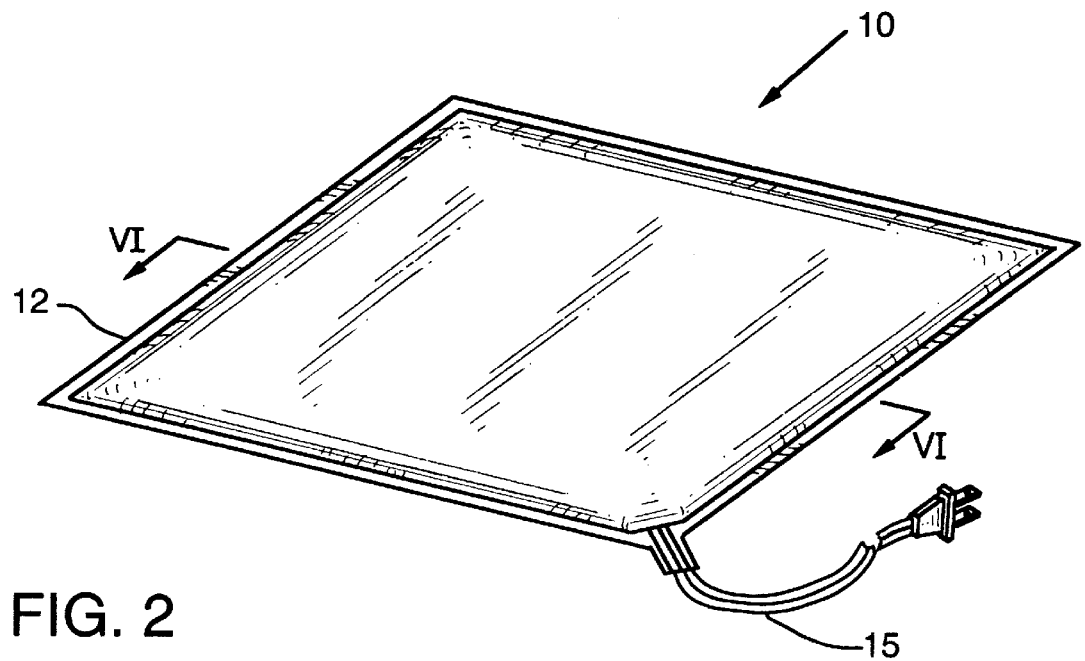
FIG. 2 is an isometric view of the heating device of the present invention.

Shown in FIGS. 1 and 2 is a preferred embodiment of the heating device 10 of the present invention. Heating device 10 comprises a top layer 1, a heat retaining fluid-filled container 2, a polymeric sheet 5, an electrical heating element 6, padding material 7, and a bottom layer 11. In addition, a cloth outer covering (not shown) may be provided that covers heating device 10, thereby providing a soft outer surface for additional comfort and safety for the user.

Top layer 1 and a bottom layer 11 of heating device 10 form an outer container 12, as shown in FIGS. 2 and 6. The outer container 12 may be constructed of any suitable liquid resistant material, including, but not limited to: polyethylene, polyester, polypropylene, cellulose esters, nylon, polyvinyl alcohol acetals, polyvinyl chloride, polyvinyl chloride acetate, polystyral, methyl methacrylate and the like. Preferably, the outer container 12 of the present invention is made of polyvinyl chloride, with the top layer 1 and bottom layer 11 being approximately 0.05 mm to 0.5 mm thick. As best shown in FIGS. 1 and 7, the top layer 1 and the bottom layer 11 of the outer container 12 have interior surfaces 1b and 11a, respectively, and exterior surfaces 1a and 11b, respectively. The top layer 1 and the bottom layer 11 of the outer container 12 are sealed, as described below, to form an inner recess for receiving the various internal layers of the heating device 10.

In the preferred embodiment of the present invention, heat retaining fluid-filled container 2 is positioned adjacent the inner surface 1b of the top layer 1 of the outer container 12. The fluid-filled container 2 consists of an upper sheet 3 and a lower sheet 4 which are constructed of any suitable liquid containing material, including, but not limited to: polyethylene, polyester, polypropylene, cellulose esters, nylon, polyvinyl alcohol acetals, polyvinyl chloride, polyvinyl chloride acetate, polystyral, methyl methacrylate and the like. Preferably, the fluid-filled container 2 is constructed of a blend of nylon and polyethylene with both the upper sheet 3 and the lower sheet between about 0.05 to about 0.5 mm thick. In a preferred embodiment, the upper sheet 3 and lower sheet 4 are substantially rectangular with dimensions of 12.5 inches by 10.5 inches. Upper sheet 3 and lower sheet 4 are secured together at their edges to form a sealed pack having an internal recess 19 which contains heat retaining material 22, as shown in FIG. 7 and described below. The upper sheet 3 and the lower sheet 4 are secured together by any suitable method, but preferably are heat sealed. When upper sheet 3 and lower sheet 4 are secured together, fluid-filled container 2 preferably has an outer border of approximately one inch which is devoid of fluid and which aids in the securement to the other internal layers. Additionally, a plurality of small heat seals or baffles (not shown), internal to the outer edges, may be distributed throughout the outer surface of the fluid-filled container 2 for increasing the strength of the heat seal and for providing additional comfort to the user.

The heat retaining material 22 within container 2 may be any conventional thermally retaining composition, but preferably is a gel for added comfort and efficient heat retention. The gel preferably is approximately 0.25 to 0.5 inches thick (on average) within recess 19, and preferably comprises, in combination, sodium acetate, water, methyl paraben and hydroxyethyl cellulose, to form a non-toxic heat retaining composition. The methyl paraben may be purchased from any available distributor, such as Prism Technologies, San Antonio, Tex. The hydroxyethyl cellulose may be purchased from any available distributor, such as Union Carbide, Danbury, Conn.

Figure 3:
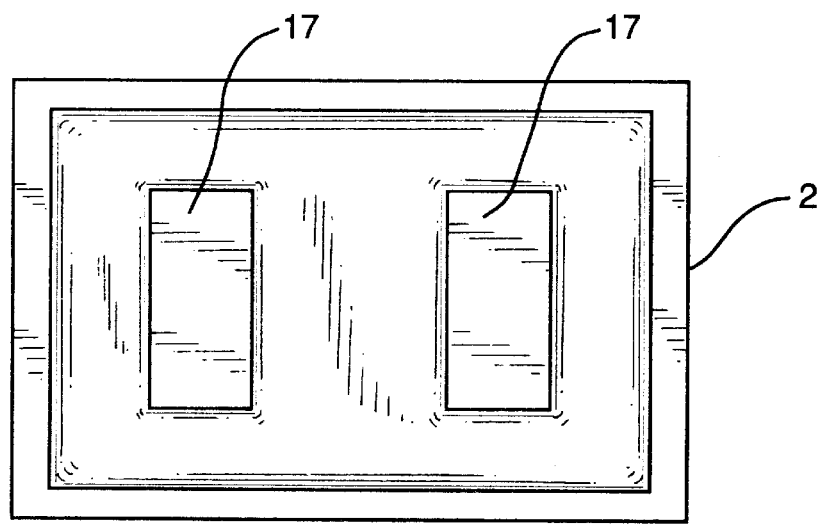
FIG. 3 is a top view of the fluid-filled container showing the internal depressions.

As best shown in FIGS. 3, 6 and 7, internal areas of upper sheet 3 and lower sheet 4 contact each other, preferably via heat sealing, to form sealed inner portions 17 within the body of fluid-filled container 2 which are devoid of heat retaining material. These internal depressions or "window panes" 17 serve several functions. First, the depressions 17 act to increase the strength of the seal between sheets 3 and 4 of the fluid-filled container 2. Second, the depressions 17 act to reduce the amount of fluid inside the fluid-filled container, thereby reducing the amount of time it takes to heat the fluid to an acceptable temperature, thereby reducing the "heat sink" effect. Finally, the depressions 17 provide areas in the vicinity of which internal thermostats 18 (FIG. 4) may be positioned to achieve more useful internal temperature readings of the heating device at the early, and most critical, stage when the fluid 22 is first being heated. As discussed below, this serves to decrease the possibility of temperature overshoot on the exterior surface 11b of the outer container 12. The positioning of depressions 17 within the body of fluid-filled container 2 can be varied so long as they coincide with the positioning of thermostats 18. In a preferred embodiment, each of depressions 17 has dimensions of approximately 4.0 inches by 1.75 inches.

As shown in FIGS. 1 and 7, polymeric sheet 5, included in the preferred embodiment of heating device 10, has a first side 5a adjacent the lower sheet 4 of the fluid-filled container 2, and a second side 5b positioned adjacent the heating element 6. The polymeric sheet 5 acts as a top cover for the heating element 6 in order to provide an additional polymeric barrier between the heating element 6 and the fluid-filled container 2, and can be constructed of any suitable polymeric material, including, but not limited to: polyethylene, polyester, polypropylene, cellulose esters, nylon, polyvinyl alcohol acetals, polyvinyl chloride, polyvinyl chloride acetate, polystyral, methyl methacrylate and the like. Sheet 5 is preferably constructed of vinyl, and is preferably approximately 0.05 mm to 0.5 mm thick.

Figure 4:
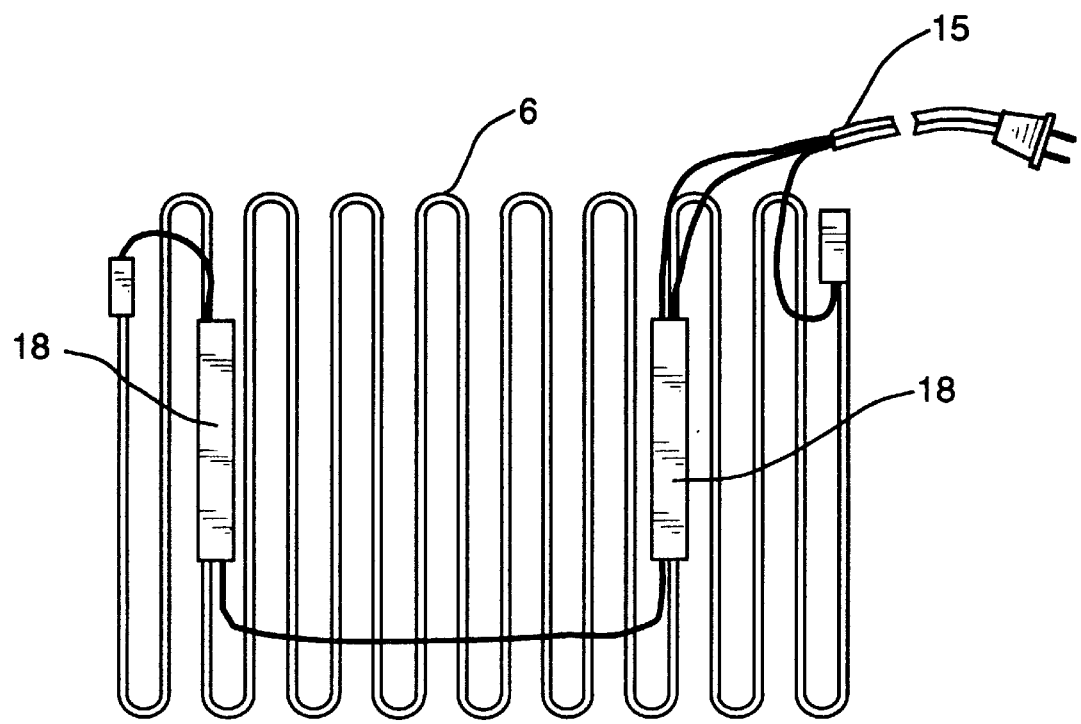
FIG. 4 is a top view of the heating element including the attached thermostats.
Figure 5:
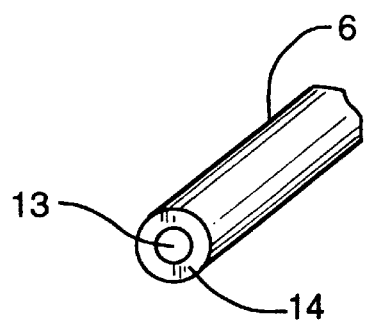
FIG. 5 is a cross sectional view of the heating element.

FIG. 4 shows a preferred embodiment of electric heating element 6 which is positioned between polymeric sheet 5 and padding material 7 of heating device 10. Heating element 6 has a serpentine configuration and, as shown in FIG. 5, is formed by a thermally conductive wire 13 coated with any heat resistant substance 14, such as a heat resistant polymer. Although not shown, it is also contemplated that the heating element 6 may be made of a positive temperature coefficient ("PTC") material. Heating device 10 of the preferred embodiment of the present invention includes a thermal regulator (not shown) that is connected in a conventional fashion to heating element 6. Connected to the thermal regulator is an external control (not shown) having various settings which enable the operator of heating device 10 to adjust the temperature and heat output. Two conventional thermostats 18 are preferably connected to the heating element 6 and are positioned to coincide with and to measure the temperature in the vicinity of depressions 17 of the fluid-filled container 2. Thermostats 18 and the thermal regulator enable heating element 6 to heat fluid 22 to a desired temperature as established by the operator via the external control, and to maintain the desired temperature throughout the remaining period of use of the heating device 10. Depressions 17 enable this temperature regulation to be achieved while minimizing the possibility of temperature overshoot on the exterior surface 11b of outer container 12 during the early stages of heating when heating element 6 is first energized.

Without depressions 17, thermostats 18 would necessarily be positioned against or in the fluid-filled container in order to be capable of obtaining representative measurements of the temperature of the fluid 22. Positioned as such, thermostats 18 would very much be influenced by the temperature of the fluid 22 at all times. As a result, during the early stages of heating when the temperature of fluid 22 is cool, thermostats 18 would cause heating element 6 to continue generating heat until enough heat was absorbed by fluid 22 so as to raise it to the desired temperature. The total amount of heat needed to raise the temperature of initially cool fluid 22 to a desired temperature is substantial and is much greater than the heat required simply to maintain fluid 22 at a constant desired temperature. By continuously providing this substantial amount of heat, heating element 6 would possibly suffer damage. Furthermore, exterior surfaces 1a and 11b would not be equally affected by this continuous and substantial amount of heat. This is because exterior surface 11b has only padding material 7 between it and heating element 6, whereas exterior surface 1a has fluid-filled container 2 between it and heating element 6. The difference in thermal conductivity and heat absorption characteristics of padding material 7 as compared to fluid 22 would cause exterior surface 11b to become undesirably hot during the early stages of heating.

Depressions 17 minimize the possibility of any such temperature overshoot by preventing thermostats 18 from being unduly influenced by the initially cool temperature of the fluid 22 during the early stages of the heating process. Instead, thermostats 18 measure the temperature of the plastic internal to and forming the depressions 17 (this plastic being more readily affected by the application of heat) which, during the early stages of heating, is higher than that of the initially cool fluid 22. Measuring temperature as such, thermostats 18 cause heating element 6 to be intermittently energized/deenergized in accordance with the temperature of depressions 17 being below/above the desired temperature, such that the temperature of the fluid 22 is caused to gradually increase over time until all of fluid-filled container 2 reaches a state of temperature equilibrium at the desired temperature. This gradual heating process, without the application of one continuous and substantial amount of heat, minimizes the possibility of temperature overshoot on exterior surface 11b, and affords greater consistency in temperature on exterior surfaces 1a and 11b in the early stages of the heating cycle. The positioning of thermostats 18 in relative close proximity to the fluid 22 also enables them to accurately monitor the temperature of fluid 22 during the other stages of the heating cycle when fluid-filled container 2 is in a state of temperature equilibrium, thus permitting reliable temperature regulation to always be achieved.

As shown in FIGS. 2 and 4, the heating element 6 is connected to a power cord 15 and, preferably, derives its power from a conventional wall outlet (not shown). The power cord 15 may be detachable from the heating device 10 for greater mobility. The heating device 10 may, alternatively, include a detachable battery pack (not shown).

As shown in FIG. 1 and discussed above, padding material 7 is positioned between heating element 6 and bottom layer 11. Positioned as such, the padding material does not interfere with the heat transfer between heating element 6 and fluid-filled container 2. Although the padding material 7 may consist of any soft, cloth-like material, it preferably consists of a layer of scrim material 8 having a front side 8a and a back side 8b, and a layer of wadding material 9, having a front side 9a and a back side 9b. The scrim material 8 provides the attachment means for the heating element 6, and in the preferred embodiment, is constructed of polyester with a thickness of approximately 0.05 to 3.0 mm. The wadding material 9 provides a layer of insulation between the heating element 6 and the bottom layer 11 of the outer container 12, and, in the preferred embodiment, is constructed of a cotton/polyester blend with a thickness of approximately 0.1 to 0.75 cm. In the preferred embodiment, the front side 8a of the scrim material 8 is adjacent to the heating element 6, and the front side 9a of the wadding material 9 is positioned adjacent to the back side 8b of the scrim material 8. The back side 9b of the wadding material 9 is adjacent to the interior surface 11a of the bottom layer 11 of the outer container 12.

In a preferred embodiment, the durability of heating device 10 is increased by securing its multiple layers together. Preferably, heating element 6, scrim material 8, and wadding material 9 are sewn together. Two polymeric strips (not shown), which are approximately 12 inches by 2.5 inches, are preferably sewn on the back side 9b of wadding material 9 thereby providing an overlapping portion of approximately 0.5 inches running substantially the length of the wadding material. The strips provide the means whereby polymeric sheet 5 is sewn to wadding material 9 thereby enclosing and securing therein heating element 6 and scrim material 8. Additionally, fluid-filled container 6 is secured, preferably sewn, to side 5a of polymeric sheet 5 and to the polymeric strips, thereby producing a securely combined internal unit. Top layer 1 and bottom layer 11 are preferably heat sealed together with one polymeric strip secured between them, enclosing and securing therein the internal layers of heating device 10 which are secured together as described above. It is also contemplated that the top layer 1 and the bottom layer 11 can form one continuous sheet which may be folded around the internal layers and heat sealed on the remaining three edges to secure therein the internal layers of heating device 10.

The multi-layered design of the heating device 10 of the present invention provides a great deal of manufacturing flexibility in that the multiple internal layers can be separately manufactured before being assembled into a completed device. This is in contrast to the prior art fluid-filled heating devices which generally must be manufactured in a single production line. Although a variety of methods of production of heating device 10 may be implemented, the preferred method of manufacture includes the first step of securing the heating element 6 to the padding material 7. Next, polymeric strips (not shown) are secured to the back side 9b of the padding material 7. Next, a polymeric sheet 5 is secured over the heating element 6 and to the strips, thereby sealing the heating element 6 inside. Next, the fluid-filled container 2 is secured to the polymeric sheet 5 to form a complete internal unit. Finally, the complete internal unit is secured inside an outer polymeric container 12, to form the completed heating device 10. In this manner, several internal layers of the present invention can be manufactured apart from the device as a whole and later attached to other layers to form the completed heating device 10.

The above description is considered that of the preferred embodiments only. Modifications of the invention may occur to those skilled in the art and to those who make or use the invention. Therefore, it is understood that the embodiments shown in the drawings and described above are for illustrative purposes and are not intended to limit the scope of protection of the invention, which is defined by the following claims as interpreted according to the principles of patent law.

What is claimed is:

1. A heating device, comprising:
 a first container having a top layer and a bottom layer, said top layer and bottom layer secured together to form a first inner recess;

a second container containing a heat retaining fluid, said second container having at least one area which is devoid of said heat retaining fluid, said second container positioned inside said first inner recess and adjacent said top layer of said first container;

an electrical heating element positioned inside said first inner recess of said first container and adjacent said second container for heating said heat retaining fluid;

at least one thermostat connected to said heating element and positioned to coincide with said at least one area in said second container; and padding material positioned inside said first inner recess and between said electrical heating element and said bottom layer of said first container.

2. The heating device of claim 1 wherein said second container comprises a first layer and a second layer secured together to form a second inner recess suitable for containing said heat retaining fluid, at least one portion of each of said first layer and said second layer secured together to form at least one depression forming said at least one area in said second container which is devoid of said heat retaining fluid.

3. The heating device of claim 1 wherein said padding material comprises a layer of scrim material and a layer of wadding material.

4. The heating device of claim 1 including a polymeric sheet positioned inside said first inner recess and between said second container and said electrical heating element.

5. The heating device of claim 1 wherein said second container said electrical heating element, and said padding material are securably positioned inside said first container.

6. The heating device of claim 4 wherein said second container said polymeric sheet, said electrical heating element, and said padding material are securably positioned inside said first container.

7. The heating device of claim 1 wherein said top layer and said bottom layer are secured by means of heat sealing.

8. The heating device of claim 2 wherein said first layer and said second layer are secured by means of heat sealing, and wherein said at least one depression is formed by means of heat sealing.

9. The heating device of claim 1 wherein said second container is secured to said heating element.

10. The heating device of claim 4 wherein said polymeric sheet is constructed of vinyl material and wherein said top layer and said bottom layer of said first container are constructed of liquid impervious vinyl material.

11. The heating device of claim 1 wherein said heat retaining fluid is a heat retaining gel.

12. A heat retaining fluid-filled container for a heating device, comprising:

a first layer and a second layer secured together to form an inner recess suitable for containing heat retaining fluid, at least one portion of each of said first layer and said second layer secured together to form at least one depression in the container which is devoid of said heat retaining fluid, said at least one depression being of sufficient size to receive a thermostat, said first and second layers being more readily affected by heat than said heat retaining liquid.

13. The heating device of claim 12 wherein said first layer and said second layer are secured by means of heat sealing, and said at least one depression is formed by means of heat sealing.

14. The fluid-filled container of claim 12 wherein said heat retaining fluid is a heat retaining gel.

15. A method of manufacturing a heating device, comprising the steps of:

securing a heating element to padding material to form a first unit;

connecting at least one thermostat to said heating element;

securing a polymeric sheet to said first unit and covering said heating element and said thermostat, thereby forming a second unit;

securing a first layer and a second layer together to form a heat retaining fluid filled container, at least one portion of each of said first layer and said second layer secured together to form at least one depression in said heat retaining fluid-filled container which is devoid of said heat retaining fluid;

securing said heat retaining fluid filled container to said polymeric sheet of said second unit such that said at least one thermostat is positioned adjacent to said at least one depression, thereby forming a third unit; and securing an outer container around said third unit.

16. The method of claim 15 wherein said outer container includes a top layer and a bottom layer, and wherein said step of securing said outer container includes heat sealing said top layer and said bottom layer together.

17. The method of claim 15 wherein said first layer and said second layer are secured by means of heat sealing, and wherein said at least one depression is formed by means of heat sealing.

* * * * *